United States Patent [19]

Miralles Medan

[11] Patent Number: 5,496,084
[45] Date of Patent: Mar. 5, 1996

[54] CONTACT LENS FITTER-REMOVER

[76] Inventor: Eliseo Miralles Medan, Ronda Zamenhof, 118 3° 1ª , Sabadell (Barcelona), Spain, 08208

[21] Appl. No.: 121,940

[22] Filed: Sep. 15, 1993

[30] Foreign Application Priority Data

Sep. 17, 1992 [ES] Spain ................................ 9201867

[51] Int. Cl.⁶ .................................................. A61F 9/00
[52] U.S. Cl. .................................. 294/1.2; 606/210
[58] Field of Search ................... 294/1.2; 606/1; 606/106, 107, 162, 205–211

[56] References Cited

U.S. PATENT DOCUMENTS

| | | | |
|---|---|---|---|
| 3,139,298 | 6/1964 | Grabiel | 606/107 |
| 3,177,874 | 4/1965 | Spriggs | 294/1.2 |
| 3,809,094 | 5/1974 | Cook | 606/210 |
| 4,079,976 | 3/1978 | Rainin et al. | |
| 4,082,339 | 4/1978 | Ross | 294/1.2 |
| 4,190,277 | 2/1980 | England | 294/1.2 |
| 4,192,204 | 3/1980 | Feldman | |
| 4,200,320 | 4/1980 | Durham | 294/1.2 |
| 4,221,414 | 9/1980 | Schrier | |
| 4,245,859 | 1/1981 | Rainin | 294/1.2 |
| 4,427,226 | 1/1984 | Shartzer | 294/1.2 |
| 4,512,602 | 4/1985 | England | 294/1.2 |

FOREIGN PATENT DOCUMENTS 1281646 10/1968 Germany .

*Primary Examiner*—Stephen C. Pellegrino
*Assistant Examiner*—Glenn Dawson
*Attorney, Agent, or Firm*—Darby & Darby

[57] ABSTRACT

The fitter-remover is comprised of a device by means of which it is possible to fit a contact lens on the user's eye and/or remove it without having to touch it with one's fingers. The device includes a body (1) with a cylindric part having a diametral notch (2), defining both legs (3) with the free ends thereof feather-edged and having a concavity (4) complementary to the convexity that the back of the corresponding lens has, body (1) which also has a flat extension opposite that cylindric part to form the handle. The device rests by means of its concave end (4) on the convex surface of the contact lens (5), the contact lens remaining adhered in order to be fit on the user's eye, while the removal is done by resting the closed legs (3) of the tweezer on the convexity of the contact lens, effecting afterwards slight pressure of the contact lens by means of transversal pressure with one's fingers, producing the detachment of the lens from one's eye.

5 Claims, 1 Drawing Sheet

5,496,084

CONTACT LENS FITTER-REMOVER

OBJECT OF THE INVENTION

As is expressed in the title of this specification, the present invention refers to a contact lens fitter-remover, which has been devised and designed to form a means or device capable of easily fitting and removing contact lens used to correct eyesight, carrying out the fitting and removing operation, logically, on and from the user's eye.

BACKGROUND OF THE INVENTION

Contact lenses are fit and removed directly with one's fingers, which implies the possibility of involuntarily dirtying or bending the contact lens, aside from there being a great risk of dropping it, with the consequential possibility of causing scratches which would make the contact lens itself useless, without eliminating the loss of the contact lens which happens on many occasions.

Up to now, the attempts made to ease the fitting and removal of contact lenses by means of auxiliary devices, in other words, without the use of the user's fingers, have not achieved adequate efficacy, so that most of the solutions made are only applicable for fitting but not for removing lenses and this as a result of the fact that the contact lens itself has a suction pad effect upon the eye surface, effect which is enhanced by the moisture that always exists in the eye area.

In this sense, there are devices comprised of a flexible or rigid duct, one of whose ends is open and defines a suction front of the lens, while the other end thereof is blind or capable of becoming obstructed by hand in order to make said suction effective. Thus, these devices, although they are relatively useful for fitting contact lenses, they are totally useless for removing them, since the adherence of the lens to the eye is always greater than the suction that the device can provide.

In view of these difficulties, devices with larger suction pads were designed, but obviously the dimensions thereof can never be larger than those of the lens itself, in such a way that in most cases these new devices could not overcome either the adherence of the lens to the eye.

In any case, the attraction that is exerted by the suction pad can be painful and harmful in the short term, thus, such devices are rejected and their use is practically non-existent.

DESCRIPTION OF THE INVENTION

The invention refers to a contact lens fitter-remover whose purpose is to avoid the above cited problems and inconveniences.

For this purpose, the fitter-remover itself is comprised of an elongated body with one part cylindrically shaped, while the other part that comprises it can be considered as a flat diametral extension of one of the bases of the cylinder comprising a handle. The cylindric part has a diametral notch which defines two parallel and relatively flexible legs, in the manner of tweezers, the free ends of said arms being inserted in a spherical concavity, similar to the roundness of conventional contact lenses, establishing a mutual adherent surface.

On the other hand, it is noteworthy that the free ends of the cited legs defined by the diametral notch of the cylindric part have a feather-edged cut, defining some ends inclined with regard to the horizontal axis of the device, although this slant can also be obtained by simple bending of the body itself which we are referring to.

In this way the lens will be fit upon the concavity defined by the free ends of the legs, and grasping the body by the extensions functioning as the handle a lens can be fit on the user's eye, remaining adhered to the eye as a result of the moisture that one's eye normally has which will serve as an adherent element which sticks to the lens.

The removal is done by resting the ends of the legs on the contact lens, closing said legs so that by means of the transversal pressure exerted by one's fingers, the lens bends slightly and thus it becomes detached from one's eye.

In order to complete the description that is going to be made hereinafter and for the purpose of providing a better understanding of the features of the invention, a set of drawings on the grounds of which the innovations and advantages of the contact lens fitter-remover, object of the invention, will be more easily understood, is attached hereto.

DESCRIPTION OF A PREFERRED EMBODIMENT

Figure 1:
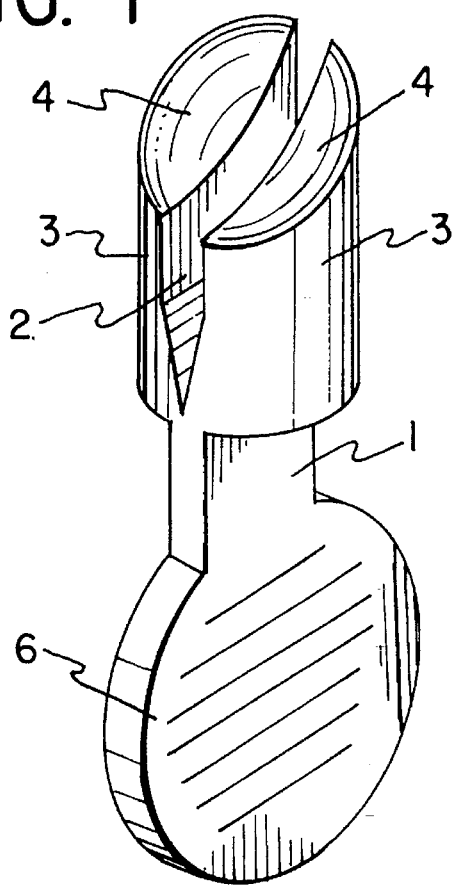
FIG. 1—It shows a general perspective view of the contact lens fitter-remover made in accordance with the object of the invention.
Figure 2:
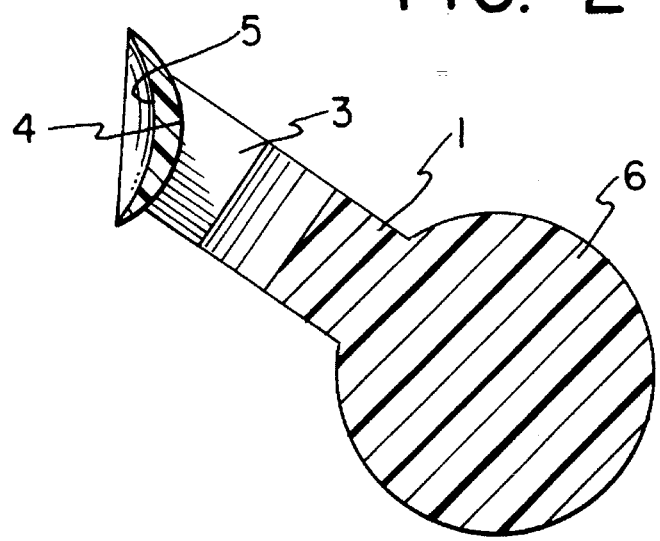
FIG. 2—It shows a longitudinal section view of the same device represented in the above figure, with a contact lens placed upon the concavity of the free end corresponding to the legs of the device.

In view of these figures, one can see how the device of the invention is comprised of an elongated body generally referred to as number (1), which in one of its end parts forms a cylindric part having longitudinally a diametral notch (2), the latter defining two parallel legs (3) which are relatively flexible, in the manner of tweezers. The free ends of these legs (3) have a round concavity (4) similar to the roundness of conventional contact lenses (5). In other words, this concavity (4) will correspond to the convexity of the contact lens itself (5) so that the latter adapts perfectly in the concave end formed by the legs (3), and thus can be applied upon the user's eye.

It has also been provided for that these free ends of the legs (3) have a slant with regard to the longitudinal axis of the device, a slant that can be obtained or achieved by means of an oblique section of the body itself or else by a bending of the same.

Opposite the above cited cylindric part, body (1) of the device or fitter-remover, defines a transversal extension (6) that is flat and has a suitable shape so as to form the handle of the device, thus making it easier to use.

In accordance with this structure of the device, when the contact lens (5) is outside the user's eye, simply resting the ends (4) of the legs (3) clamping in the back or convexity of the lens (5), the lens remains adhered to the described fitter-remover, precisely due to the shape of both elements, that is to say, due to the convexity of the contact lens itself (5) and the concavity of the cited ends (4) of the device, and besides because the contact lens (5) is wet by the soaking and cleaning liquid.

In this way, once the contact lens has become adhered to the device as it has just been stated, the lens is easily fit to one's eye, so that upon the contact surface of the lens (5) with regard to the eye being larger than the contact surface of the contact lens with the device, upon reaching one's eye the contact lens (5) remains fit to one's cornea, all without having had to touch the contact lens with one's fingers.

The removal of the lens (5) from one's eye will be done by simply resting the ends (4) of the clamping legs (3) of the device on the contact lens (5), closing the legs afterwards (3) by means of transversal pressure with one's fingers, thus obtaining a slight pressure on the lens (5) itself with the subsequent detachment from one's eye. In other words, some of the movements have an effect similar to that of removal by hand but without having to directly touch the contact lens (5) with one's fingers.

What is claimed:

1. A device for inserting and removing contact lenses comprising:

an elongated body; said elongated body comprising a substantially cylindrical elongated part;

said cylindrical part having a first end and a second end, a diametral notch extending along said cylindrical part from said first end towards said second end, said notch defining two resilient legs each having a free end, each of said free ends of said legs having a concavely curved cup-shaped surface that is configured to substantially correspond to the convexity of a convex front surface of a contact lens, said concavely curved surfaces being smooth and devoid of any projections said notch forming straight, parallel, spaced facing walls on the legs extending laterally entirely across said cylindrical part.

2. A device for inserting and removing contact lenses according to claim 1, wherein a symmetric axis of each of said concavely curved surfaces, which its corresponding perpendicular to said concavely curved surface, is disposed at an angle with respect to a longitudinal axis of elongated body.

3. A device for inserting and removing contact lenses according to claim 1, wherein said free ends of said legs are slanted such that a symmetric axis of each of said concavely curved surfaces is disposed at an angle with respect to a longitudinal axis of elongated body.

4. A device for inserting and removing contact lenses according to claim 1, wherein said elongated body includes a handle connected to said second end of said cylindrical part.

5. A device for inserting and removing contact lenses according to claim 4, wherein said handle has a flattened shape.

* * * * *